(12) United States Patent
Sukopp et al.

(10) Patent No.: US 8,115,012 B2
(45) Date of Patent: *Feb. 14, 2012

(54) PROCESS FOR PREPARING DIFLUOROMETHYLPYRAZOLYL CARBOXYLATES

(75) Inventors: Martin Sukopp, Mannheim (DE); Michael Rack, Eppelheim (DE); Sebastian Peer Smidt, Mannheim (DE); Sandra Löhr, Ludwigshafen (DE); Michael Keil, Freinsheim (DE); Jochen Dietz, Mannheim (DE); Joachim Rheinheimer, Ludwigshafen (DE); Thomas Grote, Wachenheim (DE); Thomas Zierke, Böhl-Iggelheim (DE); Jan Klaas Lohmann, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 203 days.

This patent is subject to a terminal disclaimer.

(21) Appl. No.: 12/513,003

(22) PCT Filed: Nov. 2, 2007

(86) PCT No.: PCT/EP2007/061833
§ 371 (c)(1),
(2), (4) Date: Apr. 30, 2009

(87) PCT Pub. No.: WO2008/053043
PCT Pub. Date: May 8, 2008

(65) Prior Publication Data
US 2010/0069646 A1    Mar. 18, 2010

(30) Foreign Application Priority Data
Nov. 3, 2006 (EP) .................................. 06123461

(51) Int. Cl.
*C07D 231/10* (2006.01)
*C07F 7/08* (2006.01)

(52) U.S. Cl. .................................. 548/374.1; 556/437

(58) Field of Classification Search .............. None
See application file for complete search history.

(56) References Cited

U.S. PATENT DOCUMENTS

| | | | |
|---|---|---|---|
| 5,618,951 A | 4/1997 | Britton | |
| 2006/0276656 A1 | 12/2006 | Lantzsch et al. | |
| 2008/0015244 A1 | 1/2008 | Dunkel et al. | |
| 2008/0108686 A1 | 5/2008 | Gewehr et al. | |
| 2010/0022782 A1 | 1/2010 | Zierke et al. | |
| 2010/0069646 A1 | 3/2010 | Sukopp et al. | |

FOREIGN PATENT DOCUMENTS

| | | |
|---|---|---|
| WO | WO 92/12970 | 8/1992 |
| WO | WO 93/11117 | 6/1993 |
| WO | WO 03/070705 | 8/2003 |
| WO | WO 2005/044804 | 5/2005 |
| WO | WO 2005/123690 | 12/2005 |
| WO | WO 2007/031323 | 3/2007 |
| WO | WO 2008/053043 | 5/2008 |

OTHER PUBLICATIONS

International Search Report completed Dec. 5, 2007, in International Application No. PCT/EP2006/061833, filed Nov. 2, 2007.
International Preliminary Report on Patentability from corresponding International Application No. PCT/EP2006/061833, filed Nov. 2, 2007.
English Translation of the International Preliminary Report on Patentability from corresponding International Application No. PCT/EP2006/061833, filed Nov. 2, 2007.

*Primary Examiner* — Kamal Saeed
(74) *Attorney, Agent, or Firm* — Brinks Hofer Gilson & Lione

(57) ABSTRACT

The present invention relates to a process for preparing difluoromethyl-substituted pyrazol-4-ylcarboxylates of the formula I

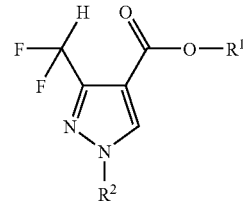

(I)

in which
$R^1$ is $C_1$-$C_8$-alkyl, $C_3$-$C_8$-cycloalkyl, $C_1$-$C_4$-alkoxy-$C_1$-$C_4$-alkyl, etc.; and
$R^2$ is hydrogen, $C_1$-$C_4$-alkyl, benzyl or phenyl,
wherein
a) a compound of the general formula II

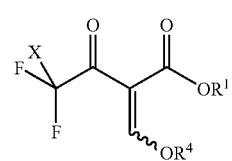

(II)

in which X is fluorine, chlorine or bromine, $R^1$ has one of the meanings given above and $R^4$ is $C_1$-$C_8$-alkyl, $C_3$-$C_8$-cycloalkyl, $C_2$-$C_8$-alkenyl, benzyl or phenyl, is reacted with a silane compound of the general formula $R^3{}_n SiCl_{(4-n)}$ in which n is 1, 2 or 3 and the substituents $R^3$ are independently of one another selected from the group consisting of $C_1$-$C_8$-alkyl and phenyl and with a metal selected from the metals of groups 1, 2, 3, 4 and 12 of the Periodic Table of the Elements having a redox potential of less than −0.7 V, based on a normal hydrogen electrode (at 25° C. and 101.325 kPa); and
b) the reaction mixture from step a) is reacted with a compound of the general formula III $R^2HN$—$NH_2$     (III)

in which $R^2$ has one of the meanings given above.

15 Claims, No Drawings

PROCESS FOR PREPARING DIFLUOROMETHYLPYRAZOLYL CARBOXYLATES

This application is a National Stage application of International Application No. PCT/EP2007/061833 filed Nov. 2, 2007, the entire contents of which is hereby incorporated herein by reference. This application also claims the benefit under 35 U.S.C. §119 of European Patent Application No. 06123461.3 filed Nov. 3, 2006, the entire contents of which is hereby incorporated herein by reference.

The present invention relates to a process for preparing difluoromethyl-substituted pyrazol-4-ylcarboxylates.

WO 92/12970 describes (3-difluoromethyl-1-methylpyrazol-4-yl)carboxamides and their use as fungicides. The preparation is carried out starting with a 2,2-difluoroacetoacetic ester which is reacted successively with triethyl orthoformate and with methylhydrazine, which gives the 3-difluoromethyl-1-methylpyrazole-4-carboxylic ester which is then hydrolyzed to give the carboxylic acid. The latter is, after conversion into the acid chloride, reacted with a suitable amine to give the corresponding amide. However, providing the 4,4-difluorinated acetoacetic ester required as starting material is comparably expensive and difficult and constitutes an obstacle for this process.

WO 2005/044804 describes alkyl esters of fluoromethyl-substituted heterocyclic carboxylic acids and their preparation by halogen exchange on corresponding chloromethyl-substituted heterocyclic carboxylic esters and their further conversion into anilides of the fluoromethyl-substituted heterocyclic carboxylic acids. However, the use of fluorinating agents is expensive, and specific requirements with a view to safety measures and the apparatus used have to be met.

Accordingly, it is an object of the present invention to provide alternative processes for preparing (3-difluoromethylpyrazol-4-yl)carboxylates and derivatives thereof starting with products whose provision is less expensive than, for example, the provision of 4,4-difluoroacetoacetic esters.

Surprisingly, it has been found that this object is achieved by reacting 4,4,4-trihalogen-substituted acetoacetic ester derivatives of formula II, defined below, with chlorosilanes in the presence of magnesium or other metals of the 1st, 2nd, 3rd, 4th or 12th group of the Periodic Table of the Elements and subsequent reaction of the reaction product with a hydrazine or hydrazine derivative.

Accordingly, the present invention provides a process for preparing difluoromethyl-substituted pyrazol-4-ylcarboxylates of the general formula I

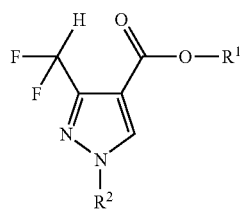

(I)

in which
R$^1$ is C$_1$-C$_8$-alkyl, C$_3$-C$_8$-cycloalkyl, C$_1$-C$_4$-alkoxy-C$_1$-C$_4$-alkyl, C$_3$-C$_8$-cycloalkoxy-C$_1$-C$_4$-alkyl, C$_2$-C$_8$-alkenyl or is benzyl which is optionally substituted by 1, 2 or 3 substituents R$^{y1}$ independently of one another selected from the group consisting of C$_1$-C$_4$-alkyl, C$_1$-C$_4$-alkoxy and nitro; and R$^2$ is hydrogen, C$_1$-C$_4$-alkyl, benzyl or phenyl, where the two last-mentioned substituents may be unsubstituted or optionally substituted by 1, 2 or 3 substituents R$^{y2}$ independently of one another selected from the group consisting of halogen, CN, nitro, C$_1$-C$_4$-alkyl, C$_1$-C$_4$-haloalkyl, C$_1$-C$_4$-alkoxy and C$_1$-C$_4$-haloalkoxy;
wherein
a) a compound of the general formula II

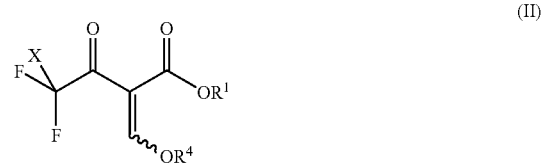

(II)

in which X is fluorine, chlorine or bromine, R$^1$ has one of the meanings given above and R$^4$ is C$_1$-C$_8$-alkyl, C$_3$-C$_8$-cycloalkyl, C$_2$-C$_8$-alkenyl, benzyl or phenyl, is reacted with a silane compound of the general formula R$^3{}_n$SiCl$_{(4-n)}$ in which n is 1, 2 or 3 and the substituents R$^3$ are independently of one another selected from the group consisting of C$_1$-C$_8$-alkyl and phenyl and with a metal selected from the metals of groups 1, 2, 3, 4 and 12 of the Periodic Table of the Elements having a redox potential of less than −0.7 V, based on a normal hydrogen electrode (at 25° C. and 101.325 kPa); and
b) the reaction mixture from step a) is reacted with a compound of the general formula III

R$^2$HN—NH$_2$ (III)

in which R$^2$ has one of the meanings given above.

The process according to the invention is associated with a number of advantages. It provides the pyrazole compound of the formula II in high yield and, in the case of the reaction with substituted hydrazines III (R$^2$≠H), in high regioselectivity. Moreover, expensive starting materials, difluoromethylcarbonyl compounds, such as 2,2-difluoroacetoacetic esters, can be dispensed with, and instead it is possible to use the much less expensive trifluoromethylcarbonyl compounds and halodifluoromethyl compounds, such as 2,2,2-trifluoroacetoacetic esters or 2-chloro-2,2-difluoroacetoacetic esters.

The terms, used in the definition of the variables, for organic groups, such as, for example, the term "halogen", are collective terms representing the individual members of these groups of organic moieties. The prefix C$_x$-C$_y$ denotes the number of possible carbon atoms in the case in question.

The term "halogen" denotes in each case fluorine, bromine, chlorine or iodine, especially fluorine, chlorine or bromine.

Examples of other meanings are:

The term "C$_1$-C$_6$-alkyl", as used herein and in the terms C$_1$-C$_6$-alkoxy, C$_1$-C$_6$-alkylamino, di(C$_1$-C$_6$-alkyl)amino, C$_1$-C$_6$-alkylthio, C$_1$-C$_6$-alkylsulfonyl, C$_1$-C$_6$-alkylsulfoxyl, C$_1$-C$_6$-alkylcarbonyl, C$_1$-C$_6$-alkoxycarbonyl and C$_1$-C$_6$-alkylcarbonyloxy, denotes a saturated straight-chain or branched hydrocarbon group comprising 1 to 6 carbon atoms, especially 1 to 4 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2- methylpropyl and their isomers. $C_1$-$C_4$-Alkyl includes, for example, methyl, ethyl, propyl, 1-methylethyl, butyl, 1-methylpropyl, 2-methylpropyl or 1,1-dimethylethyl.

The term "$C_1$-$C_6$-haloalkyl", as used herein and in the haloalkyl moieties of $C_1$-$C_6$-haloalkoxy, describes straight-chain or branched alkyl groups having 1 to 6 carbon atoms, where some or all of the hydrogen atoms of these groups are replaced by halogen atoms, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, etc.

The term "$C_1$-$C_6$-alkoxy" describes straight-chain or branched saturated alkyl groups having 1 to 6 carbon atoms, which groups are attached via an oxygen atom. Examples include $C_1$-$C_6$-alkoxy, such as, for example, methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, etc.

The term "$C_1$-$C_4$-alkoxy-$C_1$-$C_4$-alkyl", as used herein, describes $C_1$-$C_4$-alkyl radicals where one carbon atom is attached to a $C_1$-$C_4$-alkoxy radical. Examples of these are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy) butyl, 4-(1,1-dimethylethoxy)butyl, etc.

The term "$C_1$-$C_6$-alkylcarbonyl", as used herein, describes a straight-chain or branched saturated alkyl group having 1 to 6 carbon atoms which is attached terminally or internally via the carbon atom of a carbonyl unit.

The term "$C_1$-$C_6$-alkoxycarbonyl", as used herein, describes a straight-chain or branched alkoxy group having 1 to 6 carbon atoms which is attached via the carbon atom of a carbonyl unit.

The term "$C_1$-$C_6$-alkylcarbonyloxy", as used herein, describes straight-chain or branched saturated alkyl groups having 1 to 6 carbon atoms, which are attached terminally or internally via the carbon atom of the carbonyloxy unit.

The term "$C_2$-$C_6$-alkenyl", as used herein, and for the alkenyl units of $C_2$-$C_6$-alkenyloxy, describes straight-chain and branched unsaturated hydrocarbon radicals having 2 to 6 carbon atoms and at least one carbon-carbon double bond, such as, for example, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_3$-$C_{14}$-cycloalkyl", as used herein, describes mono-, bi- or polycyclic hydrocarbon radicals having 3 to 8 carbon atoms, especially 3 to 6 carbon atoms. Examples of monocyclic radicals include cyclopropyl, cyclobutyl, cyclopentyl, cyclohexyl, cycloheptyl or cyclooctyl. Examples of bicyclic radicals include bicyclo[2.2.1]heptyl, bicyclo[3.1.1] heptyl, bicyclo[2.2.2]octyl and bicyclo[3.2.1]octyl. Examples of tricyclic radicals are adamantyl and homoadamantyl.

The double bond in compound II and also in the formulae A and B defined below may have the E or the Z configuration (or the cis or trans configuration, based on the relative arrangement of the group $OR^4$ and the trifluoroacetyl radical).

In a preferred embodiment of the process according to the invention, $R^1$ in the formulae I and II is $C_1$-$C_4$-alkyl or benzyl, in particular methyl, ethyl or isopropyl; $R^1$ is especially ethyl.

For the process according to the invention, it is furthermore advantageous if $R^4$ in formula II is selected from the group consisting of $C_1$-$C_4$-alkyl and benzyl and in particular from the group consisting of methyl, ethyl, isopropyl and benzyl; $R^4$ is especially ethyl.

In formula II, X is in particular fluorine or chlorine. In a particularly preferred embodiment of the invention, X is fluorine.

$R^2$ is preferably hydrogen or $C_1$-$C_4$-alkyl; $R^2$ is especially methyl. Accordingly, the compound of the general formula III is preferably selected from the group consisting of $C_1$-$C_4$-alkylhydrazine and hydrazine; the compound of the general formula III is especially methylhydrazine or hydrazine hydrate.

All reactions described herein are carried out in reaction vessels customary for such reactions, and the reaction can be carried out either continuously or discontinuously. In general, the reactions in question will be carried out at atmospheric pressure. In the case of low-boiling solvents, the reaction in question may also be carried out under superatmospheric pressure.

Step a)

To carry out step a) of the process according to the invention, the compound of the formula II is reacted with the silane compound and with a metal of the 1st, 2nd, 3rd, 4th or 12th group of the Periodic Table having a redox potential of less than −0.7 V, based on a normal hydrogen electrode (at 25° C. and 101.325 kPa), preferably with a metal of the 1st, 2nd or 3rd main group of the Periodic Table or zinc, or especially with magnesium.

Without wishing to be tied down to any one theory, we believe that this primarily affords a silylated enol of the formula A which is possibly, depending on the chosen reaction conditions or during the work-up of the reaction or during the further reaction in step b), hydrolyzed to intermediate B.

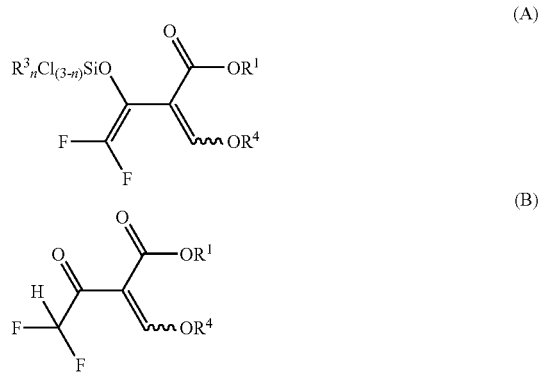

The compounds A can be detected in the reaction solution and, in some cases, they can be isolated. Accordingly, the present invention also provides the compounds A and their solutions. With respect to preferred meanings of $R^1$, $R^3$ and $R^4$ in the compounds A, what is stated above and below applies analogously.

In principle, the reaction can be carried out analogously to the reaction described in Organic Letters, 2001, 3(20), 3103-3105, which describes the preparation of 1-ethoxy-3-trimethylsilyloxy-4,4-difluorobutadiene. If X is chlorine or fluorine, the reaction can be carried out in particular analogously to the methods described in Tetrahedron Letters, 1983, Vol. 24, No. 5, 507-510. J. Chem. Soc. Perkin Trans. I, 1988, 1149-1153, J. Org. Chem. 1995, 60, 5570-5578, J. Org. Chem. 2006, 71, No. 15, 5468-5473 and U.S. Pat. No. 5,618,951.

Examples of metals of the 1st, 2nd, 3rd, 4th and 12th group of the Periodic Table of the Elements having a redox potential of less than −0.7 V, for example <−0.7 to −3.0 V, based on a normal hydrogen electrode (at 25° C. and 101.325 kPa), are alkali metals, in particular lithium, sodium or potassium, alkaline earth metals, in particular magnesium or calcium, furthermore aluminum, titanium, zirconium and zinc. Preferred metals are sodium, magnesium and zinc, and magnesium is particularly preferred, in particular when X is fluorine. Particular preference is likewise given to zinc, in particular when X is chlorine or bromine.

It has been found to be advantageous to use, in step a), a silane compound $R^3{}_n SiCl_{(4-n)}$ in which n is 2 or 3. Particularly preferably, the substituents $R^3$ in these silane compounds are independently of one another $C_1$-$C_4$-alkyl, in particular methyl, ethyl, isopropyl, tert-butyl. The compound is in particular a silane compound in which n is 3. Here, the 3 radicals $R^3$ may be identical or different, and preference is given to those silane compounds in which 2 of the radicals $R^3$ are methyl and the remaining radical $R^3$ is $C_1$-$C_4$-alkyl. In this case, the silane compound is preferably trimethylsilyl chloride, ethyldimethylsilyl chloride, dimethylpropylsilyl chloride, dimethylisopropylsilyl chloride, n-butyldimethylsilyl chloride, 2-butyldimethylsilyl chloride, (2-methylpropyl) dimethylsilyl chloride or tert-butyldimethylsilyl chloride and very particularly preferably trimethylsilyl chloride. Examples of preferred silane compounds in which n is 2 are dimethyldichlorosilane and diethyldichlorosilane. In a very particularly preferred embodiment, the silane compound $R^3{}_n SiCl_{(4-n)}$ is trimethylsilyl chloride.

The silane compound is preferably employed in at least equimolar amounts or in excess, based on the compound II, where the amount of silane compound generally does not exceed 5 mol, in particular 3.5 mol, per mole of the compound II. Preferably, from 1.1 to 3.5 mol, in particular about 1.2 to 2.5 mol, of the compounds of the silane compound are employed per mole of the compound II.

In general, the silane compound is employed in an amount of at least 0.8 mol per mole of metal. Preferably, the silane compound is employed in at least equimolar amounts or in excess, based on the metal, a relatively large excess, for example of more than 200 mol %, based on the amount of metal, generally not being required. Preferably, from 0.8 to 3 mol, in particular from 0.9 to 3 mol and especially from 1 to 2 mol of the silane compound are employed per mole of metal.

Based on the compound II, the metal is generally employed in an at least equimolar amount, for example in an amount of from 1 to 5 mol, frequently from 1.1 to 4 mol and especially from 1.5 to 3 mol, per mole of the compound II.

Step a) is preferably carried out in substantial absence of water, i.e. in a dry organic solvent. Here and below, dry means that the solvent has a water content of less than 500 ppm and in particular not more than 100 ppm. Examples of suitable organic solvents are aprotic polar solvents, for example cyclic or acyclic ethers, such as diethyl ether, tert-butyl methyl ether (MTBE), diisopropyl ether, tetrahydrofuran (THF) or dioxane, cyclic or acyclic amides, for example N—$C_1$-$C_4$-alkyllactams, such as N-methylpyrrolidone, or N-di($C_1$-$C_4$-alkyl) amides of aliphatic $C_1$-$C_4$-carboxylic acids, such as dimethylformamide or dimethylacetamide, or aprotic urea derivatives, i.e. N,N,N',N'-tetraalkylureas or N,N'-dialkylated cyclic ureas, such as N,N,N',N'-tetra($C_1$-$C_4$-alkyl)alkylureas, 1,3-di($C_1$-$C_4$-alkyl)hexahydropyrimidin-2-one or 1,3-di($C_1$-$C_4$-alkyl)imidazolin-2-one, for example tetramethylurea, 1,3-dimethylhexahydropyrimidin-2-one (dimethylpropyleneurea) or 1,3-dimethylimidazolin-2-one (DMI), and also mixtures of the solvents mentioned above. Also suitable are mixtures of the abovementioned aprotic polar organic solvents with nonpolar aprotic solvents, for example with aromatic or (cyclo)aliphatic hydrocarbons, such as toluene, xylenes, hexane, cyclohexane and the like, where in these mixtures the aprotic polar solvent preferably accounts for at least 50% by volume, in particular at least 70% by volume, of the total amount of solvent. The reaction is preferably carried out in an aprotic polar solvent selected from the group consisting of cyclic or acyclic amides, in particular N—$C_1$-$C_4$-alkyllactams, such as N-methylpyrrolidone, N-di ($C_1$-$C_4$-alkyl)amides of aliphatic $C_1$-$C_4$-carboxylic acid, such as dimethylformamide or dimethylacetamide, and aprotic urea derivatives, such as N,N,N',N'-tetra($C_1$-$C_4$-alkyl) alkylureas, 1,3-di($C_1$-$C_4$-alkyl)hexahydropyrimidin-2-one or 1,3-di($C_1$-$C_4$-alkyl)imidazolin-2-one, for example tetramethylurea, 1,3-dimethylhexahydropyrimidin-2-one (dimethylpropyleneurea) or 1,3-dimethylimidazolin-2-one (DMI), and mixtures of these solvents. Particularly preferred solvents are the aprotic urea compounds and especially DMI.

The reaction in step a) is preferably carried out at temperatures of from −10 to +60° C. Preferably, it is assured that a reaction temperature of 50° C., in particular 30° C., is not exceeded.

The reaction is carried out in a manner known per se by bringing the reagents, i.e. the compound II, the silane compound and the metal, into contact with one another, preferably in a suitable solvent in a reaction vessel, where generally the metal and, if appropriate, the silane compound are initially charged in the reaction vessel. It is advantageous for at least part of the silane compound, for example at least 20%, in particular at least 50%, and the metal to be present in an organic solvent, preferably a dry organic solvent, suitable for the reaction, in the reaction vessel prior to the addition of the compound II.

In a preferred procedure, the metal and the silane compound are initially charged in a preferably dry organic solvent suitable for the reaction. Here, the metal is typically employed in particulate form, for example in the form of turnings, powders or granules. The order in which the components are initially charged is of minor importance. If appropriate, the metal is activated. Subsequently, if appropriate with cooling to dissipate the heat of reaction, the compound of the formula II is added in pure form or as a solution, the addition rate preferably being chosen such that the temperatures stated above are, if possible, adhered to and in particular not exceeded. If a solution of the compound of the formula II is used, the concentration of compound II is typically in the range from 10 to 90% by weight, based on the total weight of the solution. The solvent used for the solution is typically the solvent used for the reaction.

In another likewise preferred procedure, the metal is initially charged in an organic solvent, preferably a dry organic solvent, suitable for the reaction and, if appropriate, is activated, and initially the silane compound and then the compound II are then added successively to the reaction vessel, it being possible to add the silane compound and the compound I in pure form or as a solution in the solvent desired for the reaction.

In a further, likewise preferred procedure, the metal is initially charged in an organic solvent, preferably a dry organic solvent, suitable for the reaction and, if appropriate, is activated, and, if appropriate, part of the silane compound, for example from 1 to 30%, is then added, and the silane compound or the residual amount of the silane compound and the compound II are then added together or via separate feeds to the reaction vessel, it being possible to add the silane compound and the compound II in pure form or as a solution in the solvent desired for the reaction.

Alternatively, it is also possible to initially charge compound II and the metal in a solvent suitable for the reaction and to add the silane compound in pure form or as a solution in the solvent suitable for the reaction.

Depending on the reactivity of the compounds II, the silane compound, the metal and the reaction temperature, the period of time over which the compound II or the silane compound is added is generally in the range from 5 to 240 minutes, frequently in the range from 10 to 120 minutes, preferably in the range from 20 to 60 minutes. If appropriate, this may be followed by a post-reaction phase of generally in the range of from 10 minutes to 360 minutes, frequently in the range of from 15 minutes to 240 minutes and in particular in the range of from 20 minutes to 180 minutes. The total reaction time (addition time+any post-reaction phase) required for complete conversion is generally in the range from 20 minutes to 10 hours, often in the range from 30 minutes to 6 hours and preferably in the range from 1 to 5 hours. The conversion of the compound II is generally quantitative or almost quantitative (>95% conversion).

It has been found to be expedient to activate the metal initially charged in the reaction vessel prior to addition of the compound II or the silane compound, for example by treatment with ultrasound or by chemical means, for example by treatment with bromine, iodine, trichloromethane or dibromomethane.

For the further reaction, the reaction mixture may be worked up and the reaction product from step a) may be isolated. The quantitative isolation of compounds of the formula A is generally carried out under weakly basic or anhydrous conditions to avoid premature hydrolysis. If the reaction mixture is worked up with addition of water, there is at least partial hydrolysis to compound B, and what is obtained is compound B, if appropriate as a mixture with compound A. A premature hydrolysis of compound A is preferably avoided.

For the reaction in step b), it is not necessary to isolate the compounds formed. In contrast, it has been found to be favorable to dispense with isolating the reaction products. Accordingly, in a preferred embodiment of the process according to the invention, the further reaction in step b) is carried out without prior isolation of reaction product A. Prior to further conversion, excess silane compound is preferably removed partially or, in particular, substantially, i.e. at least to a residual amount of less than 10 mol %, based on the compound II employed, or completely, for example by distillation. If appropriate, further volatile components of the reaction mixture, for example the solvent, are also removed partially or, in particular, completely.

The compounds of the general formula II used in step a) are commercially available or can be prepared, for example, analogously to the reaction described for (2-ethoxymethylene-4,4,4-trifluoro)acetoacetic ester in Journal of Medicinal Chemistry, 2000, Vol. 43, No. 21, from a tris(halo)acetoacetic ester VII and a suitable orthoformate VIII, in general a tri($C_1$-$C_4$-alkyl) orthoformate. The reaction is shown in the scheme below:

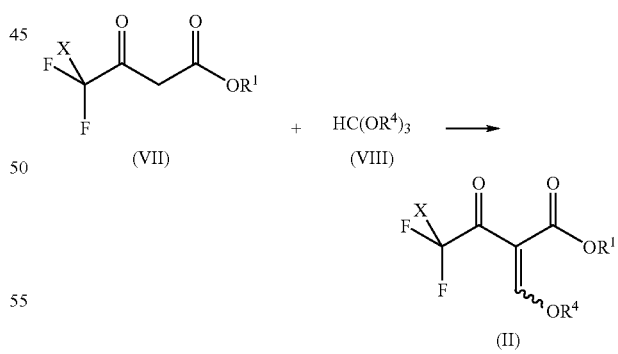

In this scheme, X, $R^1$ and $R^4$ are as defined above. A suitable orthoformate is in particular triethyl orthoformate ($R^4$=ethyl). In general, the reaction of VII with VIII is carried out such that the $C_1$-$C_4$-alkanol formed during the reaction is removed from the reaction equilibrium, for example in that it is distilled off or bound chemically, for example by carrying out the reaction in the presence of an anhydride of a carboxylic acid, for example a $C_2$-$C_4$-alkanecarboxylic acid, such as acetic anhydride.

For the reaction, the compound VIII is generally employed in excess, based on the stoichiometry of the reaction. In particular, from 1.1 to 5 mol and especially from 1.2 to 2 mol of orthoformate VIII are used per mole of compound VII.

The reaction of VII with VIII is usually carried out at elevated temperature, frequently in the range from 80 to 180° C., in particular in the range from 100 to 150° C. If appropriate, an acid, for example an organic sulfonic acid, such as p-toluenesulfonic acid, may be added as catalyst. In a preferred embodiment, the reaction of VII with the orthoformate VIII is carried out in acetic anhydride.

In general, compound II is purified prior to being used in the process according to the invention; in particular, unreacted starting materials VII and/or VIII will be removed. This can be carried out in a simple manner, for example by fractional distillation.

Step b)

The preparation of difluoromethyl-substituted pyrazol-4-ylcarboxylates of the general formula I in step b) of the process according to the invention is carried out by reacting the reaction product from step a), if appropriate after isolation or purification of the compounds obtained therein, or in particular by reacting the reaction solution obtained in step a), preferably after removal of excess silane compound, with a hydrazine compound of the formula IV.

In principle, the reaction in step b) can be carried out analogously to the reaction, described in WO 92/12970, of 3-(difluoromethyl-1-methylpyrazol-4-yl)ethylcarboxylate with methylhydrazine.

Preferably, hydrazine or a hydrazine derivative of the general formula III is employed in at least equimolar amounts or in excess, a relatively large excess of compound III, for example more than 20 mol %, based on 1 mol of the compound II employed in step a), generally not being required. Preferably, from 1.0 to 1.2 mol, in particular about 1.01 to 1.1 mol, of the hydrazine compound III are employed per mole of compound II.

The hydrazine compound of the formula III is preferably a $C_1$-$C_4$-alkylhydrazine or hydrazine or hydrazine hydrate; the compound of the general formula III is especially methylhydrazine or hydrazine hydrate.

The reaction of the reaction product from step a) with the hydrazine compound III is generally carried out such that the reaction product from step a) is mixed, preferably by adding the reaction product, if appropriate in the form of a solution in an organic solvent, for example in the form of the reaction solution, if appropriate after removal of excess silane compound, to the hydrazine compound of the formula III. The hydrazine compound of the formula III is preferably initially charged as a solution in an organic solvent or solvent/water mixture. Alternatively, the hydrazine compound of the formula III, preferably as a solution in an organic solvent or solvent/water mixture, may also be added to the reaction product from step a) or a solution thereof in an organic solvent or solvent/water mixture.

Organic solvents suitable for the reaction in step b) are, for example:

protic polar solvents, for example aliphatic alcohols having preferably 1 to 4 carbon atoms, such as methanol, ethanol, n-propanol, isopropanol, n-butanol, isobutanol or tert-butanol, aromatic hydrocarbons, such as benzene, toluene, xylenes, cumene, chlorobenzene, nitrobenzene or tert-butylbenzene, aprotic polar solvents, for example cyclic or acyclic ethers, such as diethyl ether, tert-butyl methyl ether (MTBE), tetrahydrofuran (THF) or dioxane, cyclic or acyclic amides, such as dimethylformamide, dimethylacetamide, N-methylpyrrolidone or tetramethylurea, or aliphatic nitriles, such as acetonitrile or propionitrile, and also mixtures of the solvents mentioned above.

The reaction is preferably carried out in a protic polar solvent, in particular in a $C_1$-$C_4$-alkanol and particularly preferably in methanol, ethanol, or in acetonitrile, or in a mixture of a protic polar solvent with an aprotic polar solvent or in a mixture of these solvents with water.

The reaction in step b) is preferably carried out in the presence of water. Here, even small amounts of water of 0.1% by volume, based on the total amount of solvent (organic solvent+water), are sufficient. In general, the amount of water will not exceed 50% by volume, frequently 30% by volume, in particular 15% by volume, based on the total amount of organic solvent+water, and it is frequently in the range of from 0.1 to 50% by volume, preferably in the range of from 0.5 to 30% by volume, in particular in the range of from 1 to 15% by volume, based on the total amount of organic solvent+water. In a particularly preferred embodiment of the invention, the reaction in step b) is carried out in a mixture of $C_1$-$C_4$-alkanol and water and especially in a methanol/water mixture. With respect to the volume ratios of alkanol to water, what was said above applies.

The reaction is preferably carried out at temperatures of from −80 to +100° C. In general, the upper temperature limit is the boiling point of the solvent in question, provided the reaction is carried out under atmospheric pressure. Preferably, a reaction temperature of 60° C. and in particular 40° C. will not be exceeded. For practical reasons, the reaction is frequently carried out at room temperature. In a special embodiment, initially, prior to the reaction, the temperature is set to from −60 to 0° C., in particular from −60 to −20° C., and during the reaction the reaction mixture is warmed to a temperature of from 0 to 60° C., in particular from 10 to 40° C.

Depending on the reaction temperature, the reaction time required for complete conversion is typically in the range of from 1 to 48 hours and preferably in the range of from 4 to 24 hours.

Work-up of the reaction mixture and isolation of the pyrazole compound of the general formula I are carried out in a customary manner, for example by removing the solvent, for example by distillation or by aqueous extractive work-up or by a combination of these measures. Further purification may be carried out, for example, by crystallization or by chromatography. However, frequently the product is already obtained in a purity which makes further purification steps redundant.

Step b) of the process according to the invention affords the compounds of the general formula I in good to very good yields of generally at least 70%.

The present invention furthermore provides a process for preparing a compound of the general formula IV

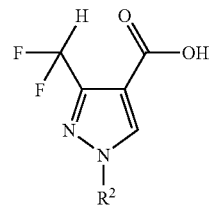

(IV)

in which $R^2$ has one of the meanings given above. The process for preparing the compound IV comprises i) providing a compound of the formula I by the process according to the invention as described and
ii) hydrolysis of the compound I.

The hydrolysis can be carried out under acid catalysis or basic or otherwise. The compound I can be employed as such, i.e. after isolation. However, it is also possible to use the reaction mixture obtained in step b), if appropriate after removal of volatile components such as solvents, without further purification for the hydrolysis.

For the basic hydrolysis of the compound I, the compound of the formula I is typically treated with an alkali metal hydroxide, such as sodium hydroxide, potassium hydroxide or lithium hydroxide, preferably with an aqueous alkali metal hydroxide solution, especially an aqueous NaOH solution or an aqueous KOH solution, until the ester is completely hydrolyzed, preferably with heating.

For the basic hydrolysis, the molar ratio of the compound of the formula I to the base is typically in the range from 0.8:1 to 1:10 and is in particular about equimolar (i.e. in the range from 0.9:1 to 1.2:1); however, a relatively large excess of base, for example up to 5 mol per mole of compound I, may also be advantageous.

The basic hydrolysis is usually carried out in a diluent or solvent. Suitable diluents or solvents are, in addition to water, also organic solvents stable toward alkali, and also mixtures thereof with water. Examples of organic solvents stable to alkali are in particular the $C_1$-$C_4$-alkanols mentioned above, and also the acyclic and cyclic ethers mentioned above. Preferably, the hydrolysis is carried out in aqueous phase, i.e. in water or in a mixture of water with one of the organic solvents mentioned above, the content of organic solvent in the aqueous phase generally typically not exceeding 30% by volume, based on the total amount of water and organic solvent.

The basic hydrolysis is preferably carried out at temperatures of from 20 to 100° C. In general, the upper temperature limit is the boiling point of the solvent used, provided the reaction is carried out under atmospheric pressure. Preferably, a reaction temperature of 100° C. and in particular 90° C. will not be exceeded. It has been found to be particularly advantageous to carry out the reaction at a temperature above the boiling point of the alcohol component of the ester. Starting with, for example, a compound of the general formula I in which $R^1$ is ethyl, the hydrolysis is preferably carried out at a temperature of at least 80° C., for example in the range from 80 to 100° C. Here, the reaction time depends on the reaction temperature, on the concentration and on the stability of the respective ester bond. In general, the reaction conditions are chosen such that the reaction time is in the range from 1 to 12 h, in particular in the range from 2 to 8 h.

The acid hydrolysis of the compound I can be carried out analogously to known acid ester hydrolyses, i.e. in the presence of catalytic or stoichiometric amounts of an acid and water (see, for example, J. March, Advanced Organic Chemistry, 2nd Ed., 334-338, McGraw-Hill, 1977 and the literature cited therein). Frequently, the reaction is carried out in a mixture of water and an aprotic organic solvent, for example an ether as mentioned above. Examples of acids are hydrohalic acids, sulfuric acid, organic sulfonic acids, such as p-toluenesulfonic acid, methanesulfonic acid, phosphoric acid, and also acidic ion exchanger resins and the like.

Suitable hydrolysis catalysts are furthermore alkali metal iodides, such as lithium iodide, trimethyliodosilane or mixtures of trimethylchlorosilane with alkali metal iodides, such as lithium iodide, sodium iodide or potassium iodide.

The isolation of the acid IV is then carried out by customary separation processes, such as, for example, precipitation by adjusting the pH, or extraction.

In an advantageous manner, the compounds of the general formula I according to the invention are suitable for synthesizing a large number of compounds which are of interest as active compounds, such as, for example, for preparing 3-difluoromethylpyrazole-4-carboxamides of the formula V defined below:

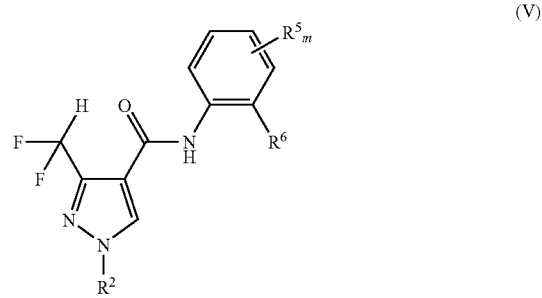

(V)

in which
$R^2$ has the meaning given above;
$R^5$ is selected from the group consisting of halogen, $C_1$-$C_6$-alkyl, $C_1$-$C_6$-alkoxy, $C_1$-$C_6$-alkylthio, $C_1$-$C_6$-haloalkyl, $C_1$-$C_6$-haloalkoxy and $C_1$-$C_6$-haloalkylthio;
m is 0, 1, 2, 3 or 4 and in particular 0 or 1;
$R^6$ is selected from the group consisting of $C_1$-$C_8$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, where the 6 abovementioned radicals are unsubstituted or may be partially or fully halogenated and/or may carry 1, 2, 3, 4 or 5 substituents $R^{ay}$, where the substituents $R^{ay}$ are independently of one another selected from the group consisting of cyano, nitro, hydroxyl, mercapto, amino, carboxyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, $C_1$-$C_6$-alkylamino, di($C_1$-$C_6$-alkyl)amino, $C_1$-$C_6$-alkylsulfonyl, $C_1$-$C_6$-alkylsulfoxyl, formyl, $C_1$-$C_6$-alkylcarbonyl, $C_1$-$C_6$-alkoxycarbonyl, formyloxy and $C_1$-$C_6$-alkylcarbonyloxy;
$C_3$-$C_{14}$-cycloalkyl or phenyl which are unsubstituted or may be substituted by 1, 2, 3, 4 or 5 radicals $R^{ax}$, where the radicals $R^{ax}$ are independently of one another selected from the group consisting of halogen, cyano, nitro, hydroxyl, mercapto, amino, carboxyl, $C_1$-$C_6$-alkyl, $C_1$-$C_6$-haloalkyl, $C_3$-$C_6$-cycloalkyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, $C_1$-$C_6$-alkylamino, di($C_1$-$C_6$-alkyl)amino, $C_1$-$C_6$-alkylsulfonyl, $C_1$-$C_6$-alkylsulfoxyl, formyl, $C_1$-$C_6$-alkylcarbonyl, $C_1$-$C_6$-alkoxycarbonyl, formyloxy and $C_1$-$C_6$-alkylcarbonyloxy.

In formula V, $R^6$ is preferably selected from the group consisting of $C_1$-$C_8$-alkyl, $C_1$-$C_8$-haloalkyl, $C_1$-$C_6$-alkoxy, $C_1$-$C_6$-haloalkoxy, phenyl and cyclopropyl, where phenyl and cyclopropyl may be substituted in the manner mentioned above. According to a particularly preferred embodiment, $R^6$ is phenyl which may optionally be substituted by 1, 2, 3, 4 or 5 radicals $R^{ax}$. $R^{ax}$ is in particular selected from the group consisting of halogen, $C_1$-$C_6$-alkoxy, $C_1$-$C_6$-alkylthio, $C_1$-$C_6$-alkylsulfonyl, $C_1$-$C_6$-alkylsulfoxyl, $C_1$-$C_6$-haloalkylthio, $C_1$-$C_6$-haloalkylsulfonyl and $C_1$-$C_6$-haloalkylsulfoxyl. $R^5$ is in particular halogen.

The process comprises providing the pyrazolecarboxylate of the formula I by the process described herein and reacting it with an amino compound of the formula VI

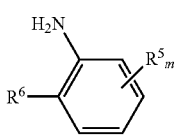

(VI)

in which m, R⁵ and R⁶ have the meanings given above; or providing the pyrazole-4-carboxylic acid of the formula IV by the processes described herein, if appropriate converting the pyrazole-4-carboxylic acid IV into its carbonyl halide IVa

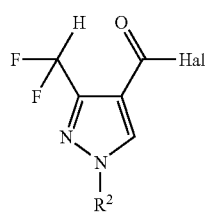

(IVa)

in which $R^2$ has the meaning mentioned above and Hal is halogen, in particular chlorine, and the subsequent reaction of the pyrazole-4-carboxylic acid of the formula IV or its carbonyl halide IVa with an amino compound of the formula VI.

Suitable methods for preparing anilides by reacting carboxylic acids or carboxylic esters with aromatic amines are known to the person skilled in the art, for example from the prior art cited at the outset, and also from J. March, Advanced Organic Chemistry, 2nd Ed., 382 f., McGraw-Hill, 1977 and Organikum, 21st Ed., Wiley-VCH, Weinheim 2001, pp. 481-484, and the literature cited therein, and these methods can be applied analogously to the preparation according to the invention of the compounds V.

For example, pyrazolecarboxylates of the formula I, in particular those where $R^1$=methyl or ethyl, can be reacted directly with the aniline compound VI in the sense of an aminolysis of a carboxylic ester. Alternatively, the pyrazolecarboxylic acid of the formula IV can be reacted directly with the aniline compound VI in the sense of an aminolysis of a carboxylic acid.

However, frequently the pyrazolecarboxylic acid of the formula IV is initially converted into its acid halide, for example its acid chloride, and the acid halide IVa is then reacted with the aniline compound VI.

Depending on the chosen synthesis route, the coupling reaction of carboxylic acid IV or carboxylic acid derivative I or IVa and aniline derivative VI can, if appropriate, be carried out in the presence of catalysts, condensing agents, acid binders and/or with removal of water, for example by azeotropic distillation.

In general, the reaction of the carbonyl halide IVa with the aniline compound VI is carried out in an inert solvent. Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also methylene chloride, dimethyl sulfoxide and dimethylformamide, particularly preferably toluene, methylene chloride and tetrahydrofuran. It is also possible to use mixtures of the solvents mentioned.

The reaction of IVa with VI is usually carried out in the presence of a base. Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate and calcium carbonate, and also alkali metal bicarbonates, such as sodium bicarbonate, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to using triethylamine and pyridine.

The bases are generally employed in equimolar amounts, based on the compound IVa. However, they can also be employed in an excess of from 5 mol % to 30 mol %, preferably from 5 mol % to 10 mol %, or—if tertiary amines are used—as solvents, if appropriate.

The starting materials IVa and VI are generally reacted with one another in equimolar amounts. In terms of yield, it may be advantageous to use an excess of IVa of from 1 mol % to 20 mol %, preferably from 1 mol % to 10 mol %, based on VI.

This reaction of the pyrazolecarbonyl halides IVa with the aniline compounds VI is usually carried out at temperatures of from −20° C. to 100° C., preferably from 0° C. to 50° C.

The reaction of the pyrazolecarboxylic acids IV with the aniline compounds VI is usually carried out in the presence of a dehydrating agent. Suitable dehydrating agents are, for example, 1,1'-carbonyldiimidazole, bis(2-oxo-3-oxazolidinyl)phosphoryl chloride, carbodiimides, such as N,N'-dicyclohexylcarbodiimide, N-(3-dimethylaminopropyl)-N'-ethylcarbodiimide, phosphonium salts, such as (benzotriazol-1-yloxy)tris(dimethylamino)phosphonium hexafluorophosphate, bromotripyrrolidinophosphonium hexafluorophosphate, bromotris(dimethylamino)phosphonium hexafluorophosphate, chlorotripyrrolidino-phosphonium hexafluorophosphate, uronium and thiuronium salts, such as O-(benzotriazol-1-yl)-N,N,N',N'-tetramethyluronium hexafluorophosphate, O-(7-azabenzotriazol-1-yl)-N,N, N',N'-tetramethyluronium hexafluorophosphate, S-(1-oxido-2-pyridyl)-N,N,N', N'-tetramethylthiuronium tetrafluoroborate, O-(2-oxo-1(2H)pyridyl)-N,N,N',N'-tetramethyluronium tetrafluoroborate, O-[(ethoxycarbonyl)cyanomethyleneamino]-N,N,N',N'-tetramethyluronium tetrafluoroborate, carbenium salts, such as (benzotriazol-1-yloxy)dipyrrolidinocarbenium hexafluorophosphate, (benzotriazol-1-yloxy)dipiperidinocarbenium hexafluorophosphate, O-(3,4-dihydro-4-oxo-1,2,3-benzotriazin-3-yl)-N,N,N',N'-tetramethyluronium tetrafluoroborate, chloro-N',N'-bis(tetramethylene)formamidinium tetrafluoroborate, chlorodipyrrolidinocarbenium hexafluorophosphate, chloro-N,N,N',N'-bis(pentamethylene)formamidinium tetra-fluoroborate, imidazolium salts, such as 2-chloro-1,3-dimethylimidazolidinium tetrafluoroborate, preferably 1,1'-carbonyldiimidazole, bis(2-oxo-3-oxazol-idinyl)phosphoryl chloride, N,N'-dicyclohexylcarbodiimide and N-(3-dimethylaminopropyl)-N'-ethylcarbodiimide.

If the reaction of the pyrazolecarboxylic acids IV with the aniline compounds VI is carried out in the presence of a dehydrating agent, preference is given to using an organic base. Suitable organic bases are, for example, tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to using triethylamine and pyridine. The bases are generally employed in an excess of from 10 mol % to 200 mol %, preferably from 50 mol % to 150 mol %, based on the compound IV.

The starting materials IV and VI are generally reacted with one another in approximately equimolar amounts. In terms of yield, it may be advantageous to use an excess of from 1 mol % to 20 mol %, preferably from 1 mol % to 10 mol %, of one of the compounds. The dehydrating agents are generally employed in an excess of from 5 mol % to 100 mol %, preferably from 5 mol % to 60 mol %, based on the compound IV.

The reaction of IV with VI is usually carried out in a solvent. Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, and also dimethyl sulfoxide and dimethylformamide, particularly preferably methylene chloride, toluene and tetrahydrofuran. It is also possible to use mixtures of the solvents mentioned.

Hereinbelow, the preparation of difluoromethyl-substituted pyrazol-4-ylcarboxylic esters and their further processing is described by way of examples.

PREPARATION EXAMPLE 1

Preparation of ethyl 2-ethoxymethylene-4,4,4-trifluoro-3-oxobutyrate

In a 500 ml four-necked flask with stirrer, 78.3 g (0.425 mol) of trifluoroacetoacetate ethyl-(4,4,4-trifluoro)-3-oxobutyrate, 103.3 g (0.638 mol) of triethyl orthoformate and 130.0 g (1.275 mol) of acetic anhydride were mixed and heated at 120° C. for 6 hours. Then, at atmospheric pressure, initially the low-boiling components were removed and the product was then distilled under reduced pressure over a column. This gave 91.8 g (yield 90%) of the title compound as a colorless liquid of a purity>98%.

PREPARATION EXAMPLE 2

Preparation of isopropyl 2-isopropoxymethylene-4,4, 4-trifluoro-3-oxobutyrate The preparation was carried out analogously to preparation example 1 using isopropyl 4,4,4-trifluoro-3-oxobutyrate and triisopropyl orthoformate.

Example 1

Preparation of ethyl 3-difluoromethyl-1-methylpyrazole-4-carboxylate

Magnesium turnings (4.9 g, 0.20 mol), trimethylsilyl chloride (TMS-Cl: 21.8 g, 0.20 mmol) and anhydrous dimethylformamide (DMF, 240 ml) were initially charged in a 500 ml three-necked flask fitted with magnetic stirrer and thermometer. The magnesium was activated by ultrasound, and ethyl 2-ethoxymethylene-4,4,4-trifluoro-3-oxobutyrate (25.3 g, 0.10 mol) was then added in an ice bath over a period of 30 min, during which the reaction temperature was kept in a range of from 0 to 10° C. After a further 60 min, excess trimethylsilyl chloride was removed under reduced pressure. In a second 500 ml three-necked flask, an aqueous methylhydrazine solution (37%, 20.8 g, 0.12 mol) and ethanol (320 ml) were initially charged at −50° C. Over a period of 60 min, the cooled reaction solution of the first reaction was added, under continued cooling. After a further 2 hours at −50° C., the reaction mixture was allowed to warm to room temperature and stirred for a further 10 hours. According to GC analysis, the reaction mixture contained ethyl 3-difluoromethyl-1-methylpyrazole-4-carboxylate (isomer a) in a mixture with ethyl 2-difluoromethyl-1-methylpyrazole-3-carboxylate (isomer b) with an isomer ratio a:b of 82:18.

The reaction mixture was then concentrated under reduced pressure. The residue was taken up in 100 ml of ethyl acetate and washed three times with saturated aqueous sodium chloride solution, the pH of which had been adjusted to pH 2 by addition of conc. hydrochloric acid. Under reduced pressure, the organic phase was freed from the solvent. The solid residue was recrystallized from hexane. Ethyl 3-difluoromethyl-1-methylpyrazole-4-carboxylate was obtained as a colorless crystalline powder (15.3 g, 70% yield, 95% purity, isomeric purity a:b=94:6).

$^1$H-NMR (d$^6$-DMSO, 400 MHz): δ=1.27 (t, 3H, J=7.1 Hz), 3.92 (s, 3H), 4.23 (q, 2H, J=7.1 Hz), 7.21 (t, 1H, J=53 Hz), 8.41 ppm (s, 1H).

Examples 1a-1e

Attempts to prepare ethyl 3-difluoromethyl-1-methylpyrazole-4-carboxylate in various solvents in the reaction of intermediate A with methylhydrazine Ethyl 2-ethoxymethylene-4,4,4-trifluoro-3-oxobutyrate, Mg and TMS-Cl were reacted in DMF analogously to example 1, and excess TMS-Cl was removed under reduced pressure. The mixture was then converted with aqueous methylhydrazine solution (37%) in various solvents into ethyl 3-difluoromethyl-1-methylpyrazole-4-carboxylate. Table 1 below shows the isomer mixtures obtained with different solvents and ratios of the reagents.

TABLE 1

| Example | Solvent type | Amount of solvent | Isomer a [%] | Isomer b [%] |
|---|---|---|---|---|
| 1a | methanol | 480 ml | 86 | 14 |
| 1b | ethanol | 320 ml | 84 | 16 |
| 1c | acetonitrile | 320 ml | 84 | 16 |
| 1d | toluene | 480 ml | 80 | 20 |
| 1e | tetrahydrofuran | 480 ml | 80 | 20 |

Example 2

Preparation of 3-difluoromethyl-1-methylpyrazole-4-carboxylic acid

The preparation was carried out analogously to example 1, but in contrast to example 1, instead of recrystallization from hexane, the solid residue obtained after aqueous extractive work-up and removal of the ethyl acetate was processed further as follows:

16 g of a 50% by weight strength aqueous sodium hydroxide solution and 100 ml of ethanol were added to the solid residue, and with stirring, the mixture was heated at reflux for 4 h. The solvent was then removed under reduced pressure and the aqueous residue obtained was adjusted to pH 1 using 10% hydrochloric acid. This caused the dicarboxylic acid to precipitate as a solid which was isolated by filtration. This gave 3-difluoromethyl-1-methylpyrazole-4-carboxylic acid as a light-brown powder.

$^1$H-NMR (d$^6$-DMSO, 400 MHz): δ=3.92 (s, 3H), 7.21 (t, 1H, J=53 Hz), 8.34 ppm (s, 1H).

Example 3

Preparation of ethyl 3-difluoromethyl-1-methylpyrazole-4-carboxylate

Magnesium turnings (4.9 g, 0.20 mol) were initially charged in a 500 ml three-necked flask fitted with magnetic stirrer and thermometer. After activation of the magnesium by etching with iodine and subsequent addition of anhydrous N-methylpyrrolidone (NMP, 240 ml) and trimethylsilyl chloride (21.8 g, 0.20 mmol), ethyl 2-ethoxymethylene-4,4,4-trifluoro-3-oxobutyrate (25.3 g, 0.10 mol) was added at a temperature in the range from 30 to 40° C. over a period of 30 min. After a further 120 min, excess trimethylsilyl chloride was removed under reduced pressure. In a second 500 ml three-necked flask, an aqueous methylhydrazine solution (37%, 20.8 g, 0.12 mol) and ethanol (320 ml) were initially charged at −50° C. Over a period of 60 min, the cooled reaction solution of the first reaction was added, under continued cooling. After a further 2 hours at −50° C., the reaction mixture was allowed to warm to room temperature and stirred for a further 10 hours. According to GC analysis, the reaction mixture contained ethyl 3-difluoromethyl-1-methylpyrazole-4-carboxylate (isomer a) in a mixture with ethyl 2-difluoromethyl-1-methylpyrazole-3-carboxylate (isomer b) with an isomer ratio a:b of 84:16. The reaction mixture was then concentrated under reduced pressure.

The product obtained was a solution of ethyl 3-difluoromethyl-1-methylpyrazole-4-carboxylate in NMP which can be purified by extraction or crystallization analogously to example 1 or hydrolyzed to the acid by boiling with aqueous sodium hydroxide solution analogously to example 2.

Example 4

Preparation of 3-difluoromethyl-1-methylpyrazole-4-carboxylic acid

Magnesium turnings (4.9 g, 0.20 mol), trimethylsilyl chloride (32.6 g, 0.30 mmol) and anhydrous 1,3-dimethyl-2-imidazolidinone (DMI, 160 ml) were initially charged in a 500 ml three-necked flask fitted with magnetic stirrer and thermometer. After activation of the magnesium with iodine, methyl 2-methoxymethylene-4,4,4-trifluoro-3-oxobutyrate (21.3 g, 0.10 mol) was added in an ice-bath over a period of 30 min, the reaction temperature being kept within a range of from 20 to 30° C. After a further 60 min at room temperature, excess trimethylsilyl chloride was removed under reduced pressure. In a second 500 ml three-necked flask, an aqueous methylhydrazine solution (37%, 14.8 g, 0.12 mol) and methanol (320 ml) were initially charged at −50° C. Over a period of 60 min, the cooled reaction solution of the first reaction was added, with cooling being maintained. After a further 2 hours at −50° C., the reaction mixture was allowed to warm to room temperature and stirred for a further 10 hours. According to GC analysis, the reaction mixture contained methyl 3-difluoromethyl-1-methylpyrazole-4-carboxylate (isomer a) as a mixture with methyl 2-difluoromethyl-1-methylpyrazole-3-carboxylate (isomer b) in an a:b isomer ratio of 90:10. The reaction mixture was then concentrated under reduced pressure. 120 g of 10% strength aqueous sodium hydroxide solution were added to the residue, and the mixture was stirred at 100° C. for 4 h. After acidification of the aqueous solution with hydrochloric acid to pH 1 and repeated extraction with MTBE, an organic solution comprising 13.4 g of the title compound (yield isomer a: 71%) was obtained. The title compound was isolated by crystallization as a light-brown solid.

Example 5

Preparation of isopropyl 3-difluoromethyl-1-methylpyrazole-4-carboxylate

Magnesium turnings (4.9 g, 0.20 mol), trimethylsilyl chloride (21.8 g, 0.20 mmol) and anhydrous dimethylformamide (DMF, 250 ml) were initially charged in a 500 ml three-necked flask fitted with magnetic stirrer and thermometer. After activation of the magnesium by ultrasound, isopropyl 2-isopropoxymethylene-4,4,4-trifluoro-3-oxobutyrate (26.8 g, 0.10 mol) was added in an ice-bath over a period of 30 min, the reaction temperature being kept in a range of from 0 to 10° C. After a further 60 min, excess trimethylsilyl chloride was removed under reduced pressure. In a second 500 ml three-necked flask, an aqueous methylhydrazine solution (37%, 20.8 g, 0.12 mol) and ethanol (320 ml) were initially charged at −50° C. Over a period of 60 min, the cooled reaction solution of the first reaction was added, with cooling being maintained. After a further 2 hours at −50° C., the reaction mixture was allowed to warm to room temperature and stirred for a further 10 hours. According to GC analysis, the reaction mixture contained isopropyl 3-difluoromethyl-1-methylpyrazole-4-carboxylate (isomer a) as a mixture with isopropyl 2-difluoromethyl-1-methylpyrazole-3-carboxylate (isomer b) in an a:b isomer ratio of 83:17.

Example 6

3-Difluoromethyl-1-methylpyrazole-4-carbonyl chloride

A solution of 293 g of 3-difluoromethyl-1-methylpyrazole-4-carboxylic acid, prepared analogously to example 2, in 700 g of toluene was heated at 90° C., and 260 g of thionyl chloride were added over a period of 3.5 h. The mixture was allowed to cool and concentrated under reduced pressure, 100 ml of toluene were added to the residue and the mixture was again concentrated under reduced pressure. The residue was distilled over a packed column at a pressure of 0.8 mbar and a head temperature of 109° C., which gave 298.4 g of the acid chloride of a purity of 99% (yield 92.1%).

Example 7

N-(3,4'-dichloro-5-fluorobiphenyl-2-yl)-3-difluoromethyl-1-methylpyrazole-4-carboxamide In a 2 l four-necked flask with stirrer and dropping funnel, 208 g (0.788 mol) of 2-amino-3',4'-dichloro-5-fluorobiphenyl (purity 97%) and 82.1 g (1.04 mol) of pyridine were dissolved in 1100 ml of dry toluene, the mixture was heated to 45° C. and 155 g (0.788 mol) of the 3-difluoromethyl-1-methylpyrazole-4-carbonyl chloride prepared according to example 6 were added over a period of 30 min via the dropping funnel. The dropping funnel was rinsed with a small amount of toluene, and the mixture was stirred at 75° C. for 1 h. The hot mixture was then extracted successively with 270 ml of a 5% by weight strength aqueous hydrochloric acid, 270 ml of a 10% by weight strength aqueous sodium bicarbonate solution and 270 ml of deionized water. With stirring, the organic phase was cooled to room temperature. The product precipitated as a solid which was filtered off with suction through a glass filter and washed with a little cold toluene (0° C.). The solid was then dried under reduced pressure. This gave 264 g of the title compound as a white solid of purity>99%.

The pyrazole-4-carboxanilides of the general formula V ($R^2$=$CH_3$) listed in table 2 were prepared analogously to example 7:

TABLE 2

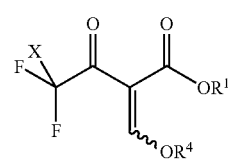

| Example | $R^5_m$ | $R^6$ | Yield [%] |
| --- | --- | --- | --- |
| 8 | 5-F | 3,4-dichlorophenyl | 88 |
| 9 | — | 1,1,2,3,3,3-hexafluoropropoxy | 89 |
| 10 | — | 1,1,2,2-tetrafluoroethoxy | 92 |
| 11 | — | 4-(methoxyiminomethyl)-3-fluorophenyl | 82 |
| 12 | — | 1,3-dimethylbutyl | 86 |
| 13 | 5-F | 4-chloro-3-fluorophenyl | 45 |
| 14 | 5-F | 3-fluoro-4-methylphenyl | 90 |
| 15 | — | 2-(cyclopropyl)cyclopropyl | 81 |
| 16 | — | 2,4-difluorophenyl | 96 |
| 17 | — | 2,5-difluorophenyl | 80 |
| 18 | — | 2,4-dichlorophenyl | 88 |
| 19 | — | 2,5-dichlorophenyl | 82 |
| 20 | — | 3,5-difluorophenyl | 79 |
| 21 | — | 3,5-dichlorophenyl | 95 |
| 22 | — | 3-fluorophenyl | 72 |
| 23 | — | 3-chlorophenyl | 79 |
| 24 | — | 2-fluorophenyl | 63 |
| 25 | — | 2-chlorophenyl | 69 |
| 26 | — | 3,4,5-trifluorophenyl | 93 |
| 27 | — | 2,4,5-trifluorophenyl | 89 |

The invention claimed is:

1. A process for preparing difluoromethyl-substituted pyrazol-4-ylcarboxylates of formula (I)

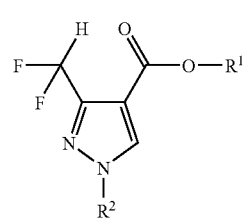

wherein
$R^1$ is $C_1$-$C_8$-alkyl, $C_3$-$C_8$-cycloalkyl, $C_1$-$C_4$-alkoxy-$C_1$-$C_4$-alkyl, $C_3$-$C_8$-cycloalkoxy-$C_1$-$C_4$-alkyl, $C_2$-$C_8$-alkenyl or is benzyl which is optionally substituted by 1, 2 or 3 substituents $R^{y1}$ independently of one another selected from the group consisting of $C_1$-$C_4$-alkyl, $C_1$-$C_4$-alkoxy and nitro; and
$R^2$ is hydrogen, $C_1$-$C_4$-alkyl, benzyl or phenyl, where the two last-mentioned substituents may be unsubstituted or optionally substituted by 1, 2 or 3 substituents $R^{y2}$ independently of one another selected from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy;
wherein
a) a compound of the general formula (II)

in which X is fluorine, chlorine or bromine, $R^1$ has one of the meanings given above and $R^4$ is $C_1$-$C_8$-alkyl, $C_3$-$C_8$-cycloalkyl, $C_2$-$C_8$-alkenyl, benzyl or phenyl, is reacted with a silane compound of formula $R^3_n SiCl_{(4-n)}$ in which n is 1, 2 or 3 and the substituents $R^3$ are independently of one another selected from the group consisting of $C_1$-$C_8$-alkyl and phenyl and
with a metal selected from the metals of groups 1, 2, 3, 4 and 12 of the Periodic Table of the Elements having a redox potential of less than −0.7 V, based on a normal hydrogen electrode (at 25° C. and 101.325 kPa); and
b) the reaction mixture from step a) is reacted with a compound of the general formula (III)

$$R^2HN-NH_2 \quad (III)$$

in which $R^2$ has one of the meanings given above.

2. The process of claim 1, wherein the metal is magnesium.

3. The process of claim 1, wherein said silane compound of the formula $R^3_n SiCl_{(4-n)}$, wherein n is 2 or 3 is employed.

4. The process of claim 1, wherein in said silane compound the substituents $R^3$ are independently of one another selected from the group consisting of $C_1$-$C_4$-alkyl.

5. The process of claim 1, wherein said silane compound is selected from the group consisting of trimethylsilyl chloride, ethyldimethylsilyl chloride, dimethylpropylsilyl chloride, dimethylisopropylsilyl chloride, n-butyldimethylsilyl chloride, 2-butyldimethylsilyl chloride, (2-methylpropyl)dimethylsilyl chloride, dimethyldichlorosilane, diethyldichlorosilane and tert-butyldimethylsilyl chloride.

6. The process of claim 1, wherein $R^4$ in formula II is selected from the group consisting of $C_1$-$C_4$-alkyl and benzyl.

7. The process of claim 1, wherein said reaction in step a) is carried out essentially anhydrously.

8. The process of claim 7, wherein said reaction in step a) is carried out in a solvent selected from the group consisting of N—$C_1$-$C_4$-alkyllactams, N-di($C_1$-$C_4$-alkyl)amides of aliphatic $C_1$-$C_4$-carboxylic acids, N,N,N',N'-tetra($C_1$-$C_4$-alkyl)alkylureas, 1,3-di($C_1$-$C_4$-alkyl)hexahydropyrimidin-2-one and 1,3-di($C_1$-$C_4$-alkyl)imidazolin-2-one.

9. The process of claim 1, wherein said reaction in step b) is carried out in the presence of water.

10. The process of claim 9, wherein said reaction in step b) is carried out in a mixture of $C_1$-$C_4$-alkanol and water.

11. The process of claim 1, wherein in formulae I and II $R^1$ is $C_1$-$C_4$-alkyl or benzyl.

12. The process of claim 1, wherein said compound of formula (III) is selected from $C_1$-$C_4$-alkylhydrazines and hydrazine hydrate.

13. A process for preparing a pyrazole-4-carboxylic acid of formula (IV)

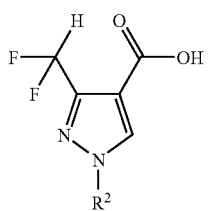

(IV)

wherein $R^2$ is hydrogen, $C_1$-$C_4$-alkyl, benzyl or phenyl, where the two last-mentioned substituents may be unsubstituted or optionally substituted by 1, 2 or 3 substituents $R^{y2}$ independently of one another selected from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy; comprising
i) the provision of a compound of formula I according to the process of claim 1, and
ii) a hydrolysis of the compound I to give the carboxylic acid IV.

14. The process of claim 13, wherein said hydrolysis is carried out in the presence of an aqueous alkali metal hydroxide solution or alkaline earth metal hydroxide solution.

15. A process for preparing pyrazole-4-carboxanilides of the general formula (V)

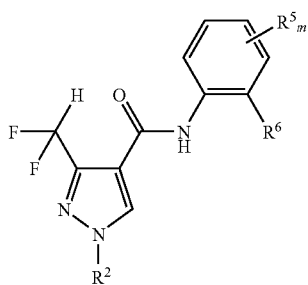

(V)

wherein
$R^2$ is hydrogen, $C_1$-$C_4$-alkyl, benzyl or phenyl, where the two last-mentioned substituents may be unsubstituted or optionally substituted by 1, 2 or 3 substituents $R^{y2}$ independently of one another selected from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy;
$R^5$ is selected from the group consisting of halogen, $C_1$-$C_6$-alkyl, $C_1$-$C_6$-alkoxy, $C_1$-$C_6$-alkylthio, $C_1$-$C_6$-haloalkyl, $C_1$-$C_6$-haloalkoxy and $C_1$-$C_6$-haloalkylthio;
m is 0, 1, 2, 3 or 4;
$R^6$ is selected from the group consisting of $C_1$-$C_6$-alkyl, $C_2$-$C_6$-alkenyl, $C_2$-$C_6$-alkynyl, $C_1$-$C_6$-alkoxy, $C_2$-$C_6$-alkenyloxy, $C_2$-$C_6$-alkynyloxy, where the 6 abovementioned radicals are unsubstituted or may be partially or fully halogenated and/or may carry 1, 2, 3, 4 or 5 substituents $R^{ay}$, where the substituents $R^{ay}$ are independently of one another selected from the group consisting of cyano, nitro, hydroxyl, mercapto, amino, carboxyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, $C_1$-$C_6$-alkylamino, di($C_1$-$C_6$-alkyl)amino, $C_1$-$C_6$-alkylsulfonyl, $C_1$-$C_6$-alkylsulfoxyl, formyl, $C_1$-$C_6$-alkylcarbonyl, $C_1$-$C_6$-alkoxycarbonyl, formyloxy and $C_1$-$C_6$-alkylcarbonyloxy;
$C_3$-$C_{14}$-cycloalkyl or phenyl which are unsubstituted or may be substituted by 1, 2, 3, 4 or 5 radicals $R^{ax}$, where the radicals $R^{ax}$ are independently of one another selected from the group consisting of halogen, cyano, nitro, hydroxyl, mercapto, amino, carboxyl, $C_1$-$C_6$-alkyl, $C_1$-$C_6$-haloalkyl, $C_3$-$C_6$-cycloalkyl, $C_1$-$C_6$-alkoxy, $C_2$-$C_6$-alkenyloxy, $C_2$-$C_6$-alkynyloxy, $C_1$-$C_6$-haloalkoxy, $C_1$-$C_6$-alkylthio, $C_1$-$C_6$-alkylamino, di($C_1$-$C_6$-alkyl)amino, $C_1$-$C_6$-alkylsulfonyl, $C_1$-$C_6$-alkylsulfoxyl, formyl, $C_1$-$C_6$-alkylcarbonyl, $C_1$-$C_6$-alkoxycarbonyl, formyloxy and $C_1$-$C_6$-alkylcarbonyloxy;
comprising:
i) the provision of a pyrazolecarboxylate of the formula I by a process of claim 1 and the reaction of the pyrazolecarboxylate of the formula I with an amino compound of the formula VI

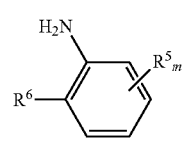

(VI)

in which m, $R^5$ and $R^6$ have the meanings mentioned above;
or
ii) the provision of a pyrazole-4-carboxylic acid of the formula IV by a process of claim 1, wherein in formulae I and II $R^1$ is $c_{1-4}$ alkyl or benzyl, if appropriate the conversion of the pyrazole-4-carboxylic acid IV into its carbonyl halide and the subsequent reaction of the pyrazole-4-carboxylic acid of the formula IV or its carbonyl halide with an amino compound of the formula VI.

* * * * *